United States Patent
Cho et al.

(10) Patent No.: US 6,964,641 B2
(45) Date of Patent: Nov. 15, 2005

(54) IMPLANTABLE MEDICAL DEVICE WITH SLEEP DISORDERED BREATHING MONITORING

(75) Inventors: Yong Kyun Cho, Maple Grove, MN (US); Eduardo N. Warman, Maple Grove, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/746,814

(22) Filed: Dec. 24, 2003

(65) Prior Publication Data

US 2005/0148897 A1    Jul. 7, 2005

(51) Int. Cl.[7] ............................................. A61B 5/08
(52) U.S. Cl. .................... 600/529; 600/587; 600/595
(58) Field of Search ............................. 600/300–301, 600/529–543, 508, 509, 587–595; 607/6, 607/8, 17–24, 47, 116, 119, 42

(56) References Cited

U.S. PATENT DOCUMENTS

| | | | |
|---|---|---|---|
| 5,038,137 A | 8/1991 | Lloyd | 340/573 |
| 5,040,536 A | 8/1991 | Riff | 128/419 PG |
| 5,233,984 A | 8/1993 | Thompson | 607/18 |
| 5,275,159 A | 1/1994 | Griebel | 128/633 |
| 5,354,317 A | 10/1994 | Alt | 607/19 |
| 5,472,453 A | 12/1995 | Alt | 607/4 |
| 5,593,431 A | 1/1997 | Sheldon | 607/19 |
| 5,630,834 A * | 5/1997 | Bardy | 607/5 |
| 5,782,884 A | 7/1998 | Stotts et al. | 607/17 |
| 5,865,760 A | 2/1999 | Lidman et al. | 600/509 |
| 5,957,957 A | 9/1999 | Sheldon | 607/17 |
| 6,044,297 A * | 3/2000 | Sheldon et al. | 607/17 |
| 6,057,767 A | 5/2000 | Barnoach | 349/575 |
| 6,104,949 A * | 8/2000 | Pitts Crick et al. | 600/547 |
| 6,126,611 A * | 10/2000 | Bourgeois et al. | 600/529 |
| 6,351,672 B1 | 2/2002 | Park et al. | 607/19 |
| 6,438,408 B1 | 8/2002 | Mulligan et al. | 600/510 |
| 6,574,507 B1 * | 6/2003 | Bonnet | 607/20 |
| 6,589,188 B1 * | 7/2003 | Street et al. | 600/538 |
| 6,741,885 B1 * | 5/2004 | Park et al. | 600/509 |
| 2002/0193697 A1 | 12/2002 | Cho et al. | 600/529 |
| 2003/0163059 A1 | 8/2003 | Poezevera et al. | 600/534 |
| 2003/0204209 A1 | 10/2003 | Burnes et al. | 607/14 |

FOREIGN PATENT DOCUMENTS

| | | | | |
|---|---|---|---|---|
| WO | WO 02/40096 A1 | 5/2002 | .......... | A61N 1/365 |
| WO | WO 2004/049930 A2 | 6/2004 | .......... | A61B 5/0205 |

* cited by examiner

Primary Examiner—Robert L. Nasser
Assistant Examiner—Patricia Mallari
(74) Attorney, Agent, or Firm—Girma Wolde Michael; Daniel G. Chapik (57) ABSTRACT

An implantable medical device (IMD) includes a sensor for monitoring parameters indicative of sleep disordered breathing. The IMD also includes a position sensor that indicates the relative position and/or activity level of the patient. The position sensor data is used in one or more ways in conjunction with the SDB sensing. The position data is used to confirm that such sensed data is likely indicative of SDB or to select the appropriate criteria for comparison.

14 Claims, 6 Drawing Sheets

IMPLANTABLE MEDICAL DEVICE WITH SLEEP DISORDERED BREATHING MONITORING

BACKGROUND OF THE INVENTION

1. Field of the Invention

The present invention relates to implantable medical devices. More specifically, the present invention relates to implantable medical devices that provide diagnosis and/or therapy for sleep disordered breathing.

2. Description of the Related Art

Sleep-disordered breathing (SDB) encompasses a variety of conditions including, for example, central sleep apnea and obstructive sleep apnea. In both instances, a cessation of breathing (apnea) and/or shallow or slow breathing (hypopnea), occurs on an intermittent or periodic basis. The apnea is generally terminated by an arousal from sleep leading to a disturbance of the sleep pattern. Such interrupted sleep often causes excessive daytime sleepiness, depression, irritability, memory impairment, and headaches. In addition, sleep-disordered breathing can be life threatening and an increasing correlation between sleep-disordered breathing and hypertension, diabetes, stroke, arrhythmia, heart failure and heart attacks is being established.

Obstructive sleep apnea is the result of a blockage of a portion of the upper airway, usually associated with a relaxation in muscle tone and/or a reduction in the size of the airway due to, for example, excessive fatty tissue. This mechanical blockage creates a pressure differential that further facilitates the apnea.

Central sleep apnea is a neurological disorder, wherein normal breathing patterns are interrupted due to a failure of the brain to generate the proper muscle stimulation pulses. Once initiated, the resultant apnea is eventually terminated with a resumption of respiration. Central sleep apnea can precede obstructive sleep apnea and this combination is referred to as mixed sleep apnea.

One particular variant of central sleep apnea that is often associated with patients suffering from chronic heart failure is Cheyne-Stokes respiration. Cheyne-Stokes respiration is a pattern of breathing characterized by a waxing and waning of tidal volume with complete cessation of breathing. Typically, a cycle of Cheyne-Stokes respiration lasts about 30–90 seconds. The cycle then repeats itself.

There are a variety of treatment options available for addressing sleep-disordered breathing. The most common treatment is the use of CPAP (Continuous Positive Airway Pressure). The patient generally wears an appliance such as a full facemask or more typically a nose covering mask or nasal inserts that deliver pressurized air into the airway to maintain the airway in an open state. The therapy is effectively a pneumatic stent. CPAP is generally effective at treating both central and obstructive apnea; however, many patients do not tolerate the therapy and discontinue its use.

Another method used to address sleep-disordered breathing involves atrial overdrive pacing (AOP). That is, an implantable medical device (IMD) is implanted to pace the heart. The pacing rate is elevated from a normal resting or sleeping rate (e.g., normal nocturnal intrinsic rate or a normal paced sleeping rate). For example, such techniques are described in U.S. Pat. No. 6,126,611, assigned to Medtronic, Inc., which is herein incorporated by reference in its entirety.

The use of AOP to address sleep-disordered breathing and its exact mechanisms are currently being investigated. The elevated pacing rate may lead to arousal such that apnea is terminated; however, it is believed more likely that the maintenance of heart rate and the increase in cardiac output achieved via AOP may positively affect autonomic tone sufficiently to reduce the overall number of apneas without causing arousals. While promising, the use of AOP does not always provide a successful therapy for sleep-disordered breathing.

There are various other therapies that can be delivered by an IMD to interrupt, terminate, or prevent episodes. Such therapies include, for example, variations in cardiac pacing, neural stimulation, muscle stimulation, patient alerts, and working in conjunction with an external device, such as the CPAP machine to tailor therapy.

In delivering such therapies, the IMD typically responds to a determination that sleep disordered breathing is present. In a broad sense, this could include simply delivering a given therapy whenever the patient is asleep (detected) or presumed asleep (night time hours). In that case, the patient would be evaluated in a lab and found to have sleep disordered breathing. The IMD would then be appropriately programmed.

More likely, the IMD would include one or more sensors that identify indicators of sleep disordered breathing. The sensors could be directly coupled with the device or communicate remotely via telemetry For example, impedance sensors could be used to monitor minute ventilation for breathing patterns. Similarly, air flow or temperature sensors could also monitor breathing. Heart rate, blood oxygen levels, or carbon dioxide levels are other indicators that can be monitored and correlated to sleep disordered breathing events.

Thus, the IMD gathers data to identify the onset of sleep disordered breathing and then responds. Alternatively, the data is used to pattern and/or predict the onset of SDB and provide the therapy accordingly. Some difficulty exists in accurately identifying SDB events. For example, variations in heart rate during sleep may indicate SDB events whereas the same variations during the day may result from intermittent exertion. Thus, there is continued need to further improve the accuracy of sleep disordered breathing event detection.

BRIEF SUMMARY OF THE INVENTION

The present invention, in one embodiment, is an IMD that incorporates a posture or position sensor and an SDB event sensor. The posture sensor is used as a confirmation that a detected event is SDB related; thus, eliminating a number of false positives. In addition, the posture data can be used to vary the therapy delivered. For example, SDB events are more likely to occur while the patient lies on their back. Thus, therapy can be initiated, augmented, intensified or otherwise varied based on such a determination.

In one embodiment, the IMD monitors for SDB events. Upon the detection of an indicator of an SDB event, the IMD determines the patient's posture to either confirm the likelihood that the event is related to SDB or to rule it out as such.

In another embodiment, the IMD monitors posture data and only evaluates or considers the SDB data when the patient is indicated to be in a proper position. For example, SDB detection is only enabled when the patient is prone, supine, laying on their side (lateral), reclined beyond a predetermined angle, etc. Thus, SDB detection is set to an inoperative status while the patient is upright, active, etc. so that events that would otherwise indicate a false positive are effectively ignored.

In one embodiment, the present invention is an implantable medical device (IMD) comprising means for sensing a physical parameter relevant to sleep disordered breathing (SDB) and means for sensing a patient position. The IMD also includes means for determining if the physical parameter is indicative of SDB based on the sensed patient position.

The present invention also includes a method of using an implantable medical device (IMD) for the detection of sleep disordered breathing in a patient. The method includes sensing a parameter indicative of SDB, determining an orientation of the IMD indicative of a position of a patient; and evaluating the sensed parameter based upon the determined orientation to determine if SDB is present.

In another embodiment, the present invention is an implantable medical device comprising a microprocessor and a position sensor coupled with the microprocessor and proving data indicative of a patient position. The IMD also includes a sleep disordered breathing (SDB) sensor communicatively coupled with the microprocessor and configured to sense a physical parameter that is useful in monitoring SDB and provide data to the microprocessor indicative of the physical parameter, wherein the microprocessor evaluates the data from the SDB sensor in a first manner if the position sensor indicates a first position and evaluates the data in a second manner if the position sensor indicates a second position.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1:
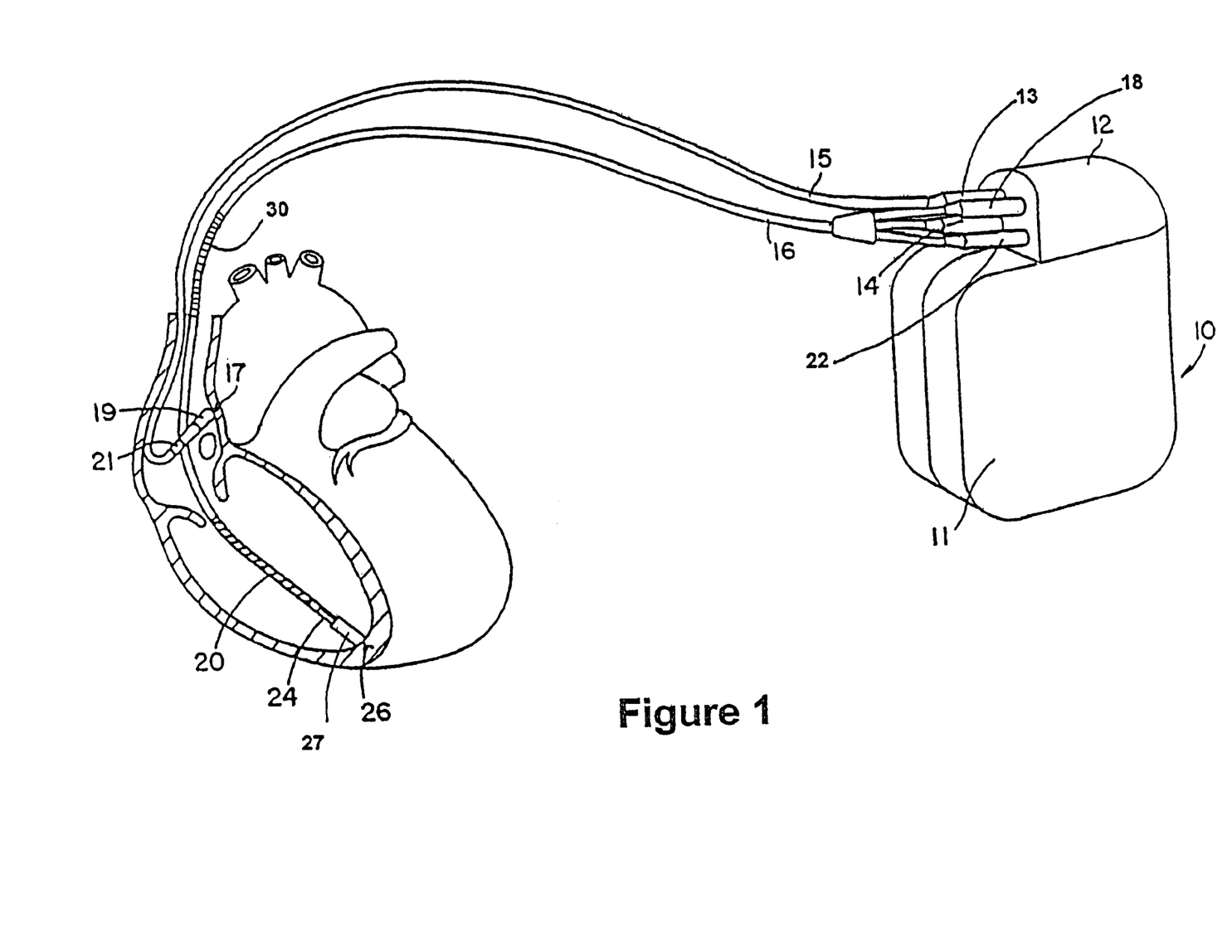
FIG. 1 is an illustration of an ICD type system according to the present invention.

Referring now to FIG. 1, there are illustrated an ICD 10 and leads 15 and 16, making up the system. ICD 10 is an implantable cardioverter defibrillator. It should be appreciated that such a device may include pacing, defibrillation, cardioversion, and/or other therapies alone or in any combination. The leads shown are illustrative, it being noted that other specific forms of leads are within the scope of this invention. Ventricular lead 16 as illustrated has, located adjacent to the distal end, an extendable helix electrode 26 and a ring electrode 24, the helix electrode being mounted retractably within an insulative head 27. Electrodes 24 and 26 are used for bipolar ventricular pacing and for bipolar sensing of ventricular depolarizations. While electrodes 24 and 26 may be used for bipolar pacing and sensing, electrode 26 may be used in conjunction with the surface of device casing 10, which surface acts as a common or indifferent electrode in what is termed unipolar operation. Ventricular lead 16 also carries a coil electrode 20, sometimes referred to as the RV (right ventricular) coil, for delivering defibrillation and/or cardioversion pulses. Coil electrode 20 is positioned on lead 16 so that when the distal tip is at the apex of the ventricle, coil 20 is positioned in the right ventricle. Lead 16 may also carry, optionally, an SVC coil 30, which can be used for applying cardioversion pulses. Lead 16 carries respective concentric coil conductors (not shown), separated from one another by appropriate means such as tubular insulative sheaths and running the length of the lead for making electrical connection between the ICD device 10 and respective ones of electrodes 20, 24, 26 and 30.

Atrial lead 15 as illustrated includes an extendable helix electrode 17 and a ring electrode 21, the helix electrode being mounted retractably within an insulative head 19. Electrodes 17 and 21 are used for bipolar atrial pacing and for sensing atrial depolarizations. While electrodes 17 and 21 may be used for bipolar pacing and sensing, electrode 17 may be used in conjunction with the surface of device casing 10, which surface acts as a common or indifferent electrode in what is termed unipolar operation. Note that, in this example, atrial lead 15 is not equipped with coils for use in the sensing and delivery of cardioversion of defibrillation pulses. This is not meant to preclude the inclusion of such applications that may be used advantageously with the present invention.

An ICD device 10, is shown in combination with atrial and ventricular leads, with the lead connector assembly 13, 14, 18, and 22 being inserted into the connector block 12 of the device 10. A specific example of a defibrillation pulse generator that may be used in conjunction with the present ventricular lead is disclosed in U.S. Pat. No. 4,953,551. Other ICD type units can be used; reference is made to U.S. Pat. Nos. 5,163,427 and 5,188,105 as disclosing illustrative forms of apparatus for delivering cardioversion and defibrillation pulses. As used herein, the term "ICD type" device refers to any device that can apply both pacing therapy and shock therapy for controlling arrhythmias.

Figure 2:
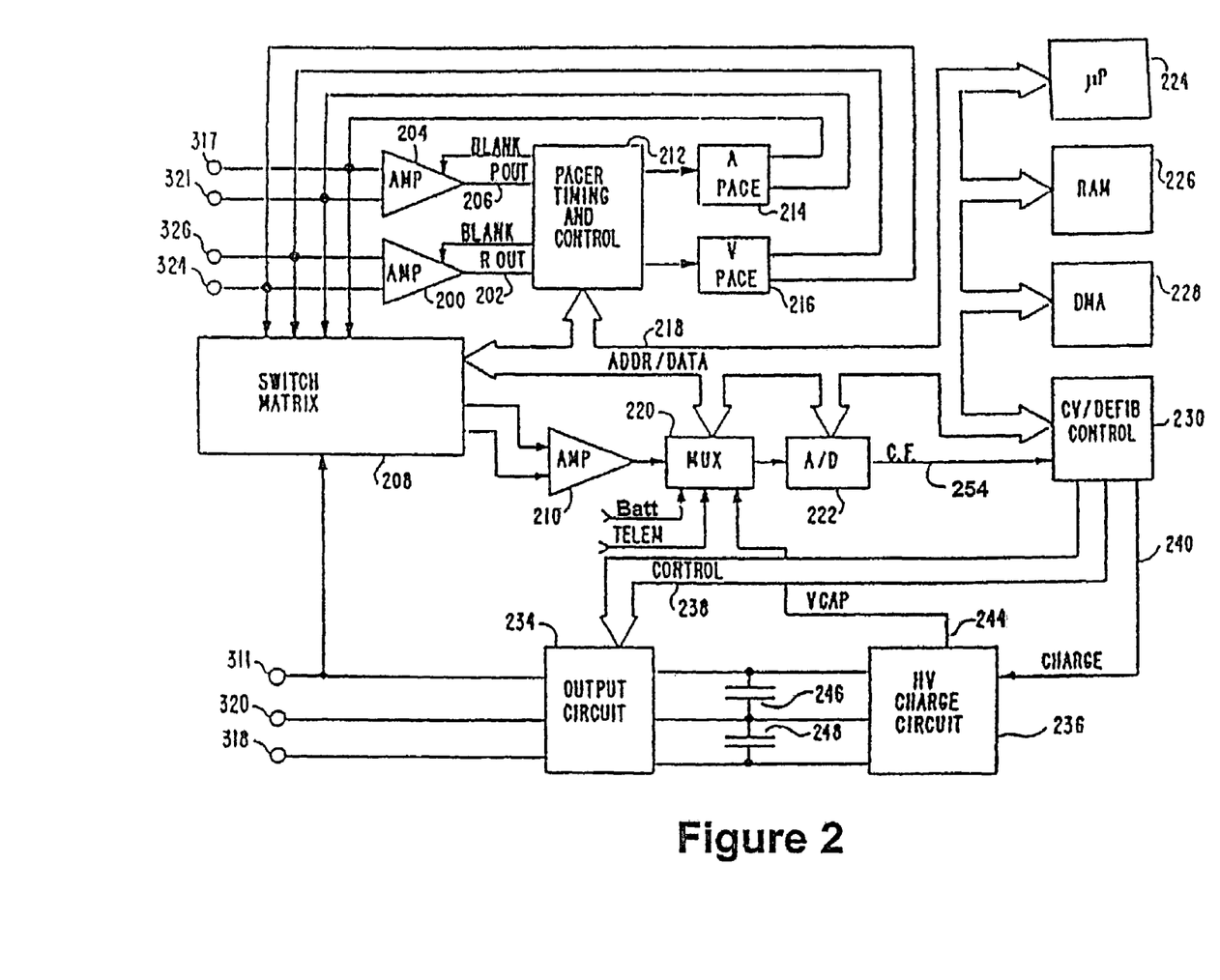
FIG. 2 is a block, functional diagram of an ICD type device adapted to carry out the features of the present invention.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such as nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 16, and is the uninsulated portion of the housing of the implantable pacemaker/cardioverter/defibrillator. Electrode 320 corresponds to electrode 20 and is a defibrillation electrode located in the right ventricle. Electrode 318 corresponds to electrode 30 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves will not restart the escape pacing interval timing. The durations of these intervals are determined by microprocessor 224, in response to stored data in memory 226 and are communicated to the pacing circuitry 212 via address/data bus 218. Pacer circuitry 212 also determines the amplitudes and pulse widths of the cardiac pacing pulses under control of microprocessor 224.

During pacing, the escape interval timers within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval timers are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval timers when reset by sensed R-waves and P-waves may be used to measure the durations of R-R intervals, P-P intervals, P-R intervals, and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the ICD may include prior art tachyarrhythmia detection algorithms. As described below, the entire ventricular arrhythmia detection methodology of presently available Medtronic pacemaker/cardioverter/defibrillators is employed as part of the arrhythmia detection and classification method according to the disclosed preferred embodiment of the invention. However, any of the various arrhythmia detection methodologies known to the art, as discussed in the Background of the Invention section above might also be usefully employed in alternative embodiments of the ICD.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval timers therein and to define refractory periods during which detection of R-waves and P-waves is ineffective to restart the escape interval timers. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval timer to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Pat. Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the physician, from a menu of therapies that are typically provided, programs the specific therapies into the device. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected for subsequent delivery. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is below a preset threshold. The references cited above in conjunction with descriptions of prior art tachycardia detection and treatment therapies are applicable here as well.

In the event that fibrillation is identified, the typical therapy will be the delivery of a high amplitude defibrillation pulse, typically in excess of 5 joules. Lower energy levels may be employed for cardioversion. As in the case of currently available ICDs, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3:
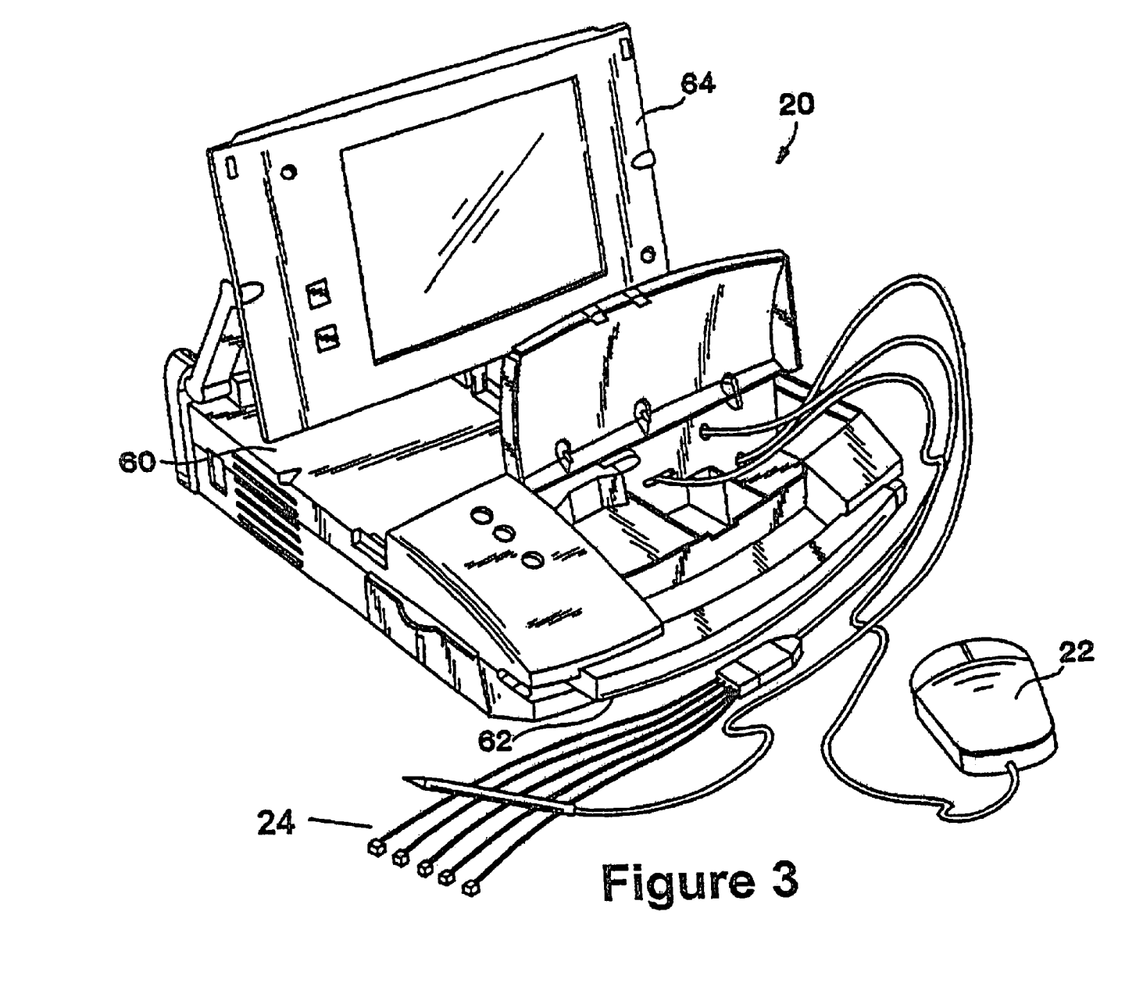
FIG. 3 is a perspective view of the external programming unit of FIG. 1.

FIG. 3 is a perspective view of programming unit program 20 in accordance with the present invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 3, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system, heart rhythm, electrical activation and a number of other parameters. Normally, programmer 20 is equipped with external ECG leads 24.

Programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 3, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled Portable Computer Apparatus With Articulating Display Panel, which patent is hereby incorporated herein by reference in its entirety. The Medtronic Model 9790 programmer is the implantable device-programming unit with which the present invention may be advantageously practiced.

Figure 4:
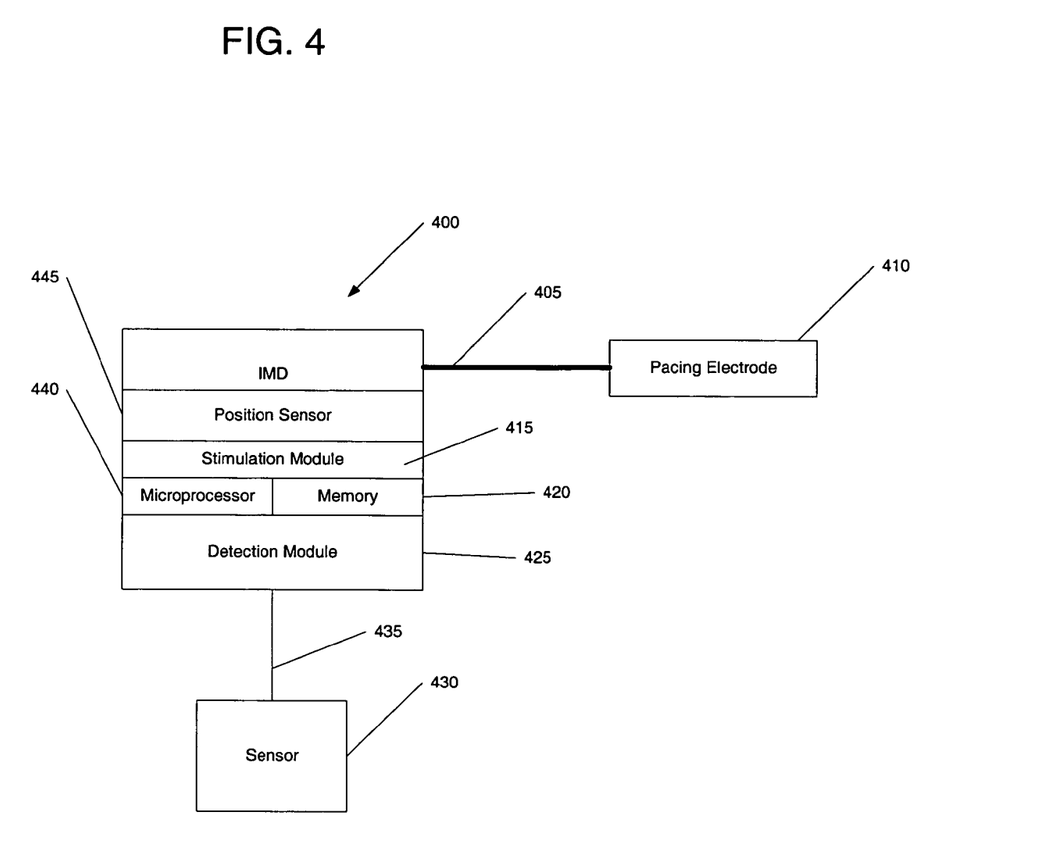
FIG. 4 is a schematic diagram of an implantable medical device useful for detecting SDB, consistent with the principles of the present invention.

FIG. 4 is a schematic illustration of an implantable medical device (IMD) 400 configured to detect SDB events and deliver appropriate therapies. In one embodiment, IMD 400 is configured as ICD 10, previously described. IMD 400 may include a wide variety of functions such as cardioversion, defibrillation, drug delivery, sensing, monitoring, recording, and remote communication such as via telemetry. If IMD 400 is equipped to provide cardiac stimulation for, e.g., pacing and/or SDB therapy, then IMD 400 delivers electrical stimulation to cardiac tissue at appropriate points in the cardiac cycle. This is most commonly accomplished via a pacing lead 405 having a pacing electrode 410 that is proximate or in contact with cardiac tissue. Of course, additional leads could be provided for other purposes including dual, triple, and quadruple sensing/pacing and defibrillation. Similarly, such electrical stimulation could be delivered to other portions of the body, including for example, the brain, nerves, muscles, or other appropriate tissue. In such a case, the appropriate leads and electrodes are provided.

The IMD 400 includes a stimulation module 415 for delivering the appropriate electrical stimulation at the appropriate time. Such functions could be carried out by separate components as well. The timing is based on data sensed through the lead 405 relative to the cardiac cycle and data acquired from a microprocessor 425 relating to traditional pacing (if applicable). A memory 420 is provided for storing algorithms available to the microprocessor 425 for delivering the appropriate therapy. The IMD 400 also includes a detection module 425 and a sensor 430 for gathering the requisite data and providing those parameters to the microprocessor 440.

One potential indicator for SDB events includes heart rate. As such, lead 405 would provide an appropriate sensor. Other leads used with the ICD 400 could likewise provide other sensor data. Alternatively, various other sensors 430 would be implanted or coupled externally to the patient and provide data to the detection module 425, either through a hard-wired connection (e.g., a lead 435) or via telemetry or some other wireless communication protocol. Sensor 430 could be an impedance based sensor for monitoring minute ventilation, a mechanical or temperature sensor for monitoring air flow (breathing) or chest movement, an oxygen sensor, a carbon dioxide sensor, a chemical sensor for monitoring a derivative indicative of oxygen or carbon dioxide, a pressure sensor for monitoring blood pressure either internal or external to the heart or sensing air flow (breathing), a microphone for monitoring breath sounds, one or more neural sensors for monitoring brain activity, or any other sensor capable of monitoring a parameter indicative or predictive of the occurrence of apnea or hypopnea, the onset of apnea or hypopnea, or any other SDB event indicator. IMD 400 may also be used in combination with an external device, such as a CPAP machine. Thus, IMD 400 may communicate with such a device, thereby receiving data and/or sending data relating to sensed parameters and/or therapy delivery (e.g., CPAP pressure, rate, effectiveness, etc.).

The sensing of and/or delivery of therapy for SDB may be a primary function, wherein IMD 400 is a dedicated device for that purpose. Alternatively, IMD 400 provides various other therapies (e.g., pacing, defibrillation, monitoring, drug delivery, etc.) and SDB monitoring/therapy is an available option.

Thus, IMD 400 is equipped to sense one or more parameters through one or more sensors 430 that are indicative of an SDB event. Upon determining the presence or the likely presence of SDB, the appropriate therapy can be delivered and/or this information can be recorded or sent to another device.

As previously discussed, the parameters sensed by sensor 430 or electrode 410 may falsely indicate the presence of SDB. For example, variations in heart rate could indicate SDB, or they could indicate variations in patient activity. Similarly, the other sensed parameters could have non-SDB related causes.

IMD 400 includes a position sensor 445. Position sensor 445 is any sensor or combination of sensors that indicates a relative body position of the patient (e.g., prone, supine, laying on side, upright, sitting, reclining, etc). In addition, position sensor 445 could also include an activity sensor or activity sensor component to indicate patient movement and activity. The position sensor 445 could use a single component for sensing both position and activity, such as an accelerometer, or separate components may be provided. Various devices are available for sensing position and/or activity. For example, position has been used to determine certain cardiac pacing regimes in heart failure patients. Activity sensors are known and used for rate-responsive pacing.

The following references illustrate various position and/or activity sensors, all of which are herein incorporated by reference in their entireties: U.S. Pat. No. 5,233,984, issued to Thompson on Aug. 10, 1993; U.S. Pat. No. 5,472,453, issued to Alt on Dec. 5, 1995; U.S. Pat. No. 5,593,431, issued to Sheldon on Jan. 14, 1997; U.S. Pat. No. 5,782,884, issued to Stotts et al. on Jul. 21, 1998; U.S. Pat. No. 5,865,760, issued to Lidman et al. on Feb. 2, 1999; and U.S. Pat. No. 5,957,957, issued to Sheldon on Sep. 28, 1999. The particular configuration of the position sensor 445 is not critical, so long as the desired position data and/or activity data is made available to the IMD 400.

Thus, the position sensor 445 provides data to the IMD 400 indicative of the relative position of the patient. In addition, position sensor 445 may provide data indicative of an activity level of the patient.

The IMD 400 makes use of the position sensor data in one or more ways. The position data is used to confirm that other sensed data is in fact likely related to SDB and rules out likely false-alarms. For example, the above referenced variations in heart rate will be deemed SDB related if the patient is prone or prone and inactive. Of course, this does not preclude the use of additional data checks, such as a determination of a sleep state or using the time of day. Alternatively, the position data is used as a prerequisite. That is, SDB monitoring will only occur when the patient is determined to be in a predetermined positions (e.g., prone, supine, reclined to some degree, inactive for some period of time, or any combination of position and/or activity that indicates a likelihood of sleep). Thus, any sensed data will then be associated with SDB, until the position data indicates the patient is no longer in one of the predetermined positions.

The IMD 400, in some embodiments, also monitors the presences of certain SDB parameters when the position/activity data indicates that the patient is not likely sleeping. That is, certain SDB sensed parameters may indicate other medical concerns or issues when the occur outside of periods of sleep. For example, Cheyne-Stokes respiration is relevant to sleep apnea. However, when the same Cheyne-Stokes respiration is detected during wakeful periods, it may indicate a negative prognosis for heart failure and may also serve as an indicator for severity as the condition progresses. Thus, even when the position/activity sensor 445 rules out other sensed data for SDB purposes, that sensed data may then be used in other ways. In some cases, the fact that SDB has been ruled out by the position/activity sensor 445, gives that sensed data additional meaning and/or relevance.

The position sensor 445 is also used to adjust the SDB sensing parameters in certain embodiments. That is, the position of the patient's body can affect a variety of sensed parameters. Thus, the IMD 400 determines the patient's position and adjusts the sensed parameter levels accordingly. For example, minute ventilation is one sensed parameter that indicates SDB. One sensor used to monitor minute ventilation is an impedance sensor that monitors transthoracic impedance variations and correlates this data to ventilation. The measured impedance amplitude (peak to peak) will vary depending on the position of the patient. For example, the measured amplitude can vary by a factor of 2–3 when the patient is laying on their side versus a prone or supine position. Patient position also often affects noise levels present in the sensor data. Thus, by incorporating the position data, the IMD 400 correlates the various sensed parameters to a relevant set of analysis criteria.

Figure 5:
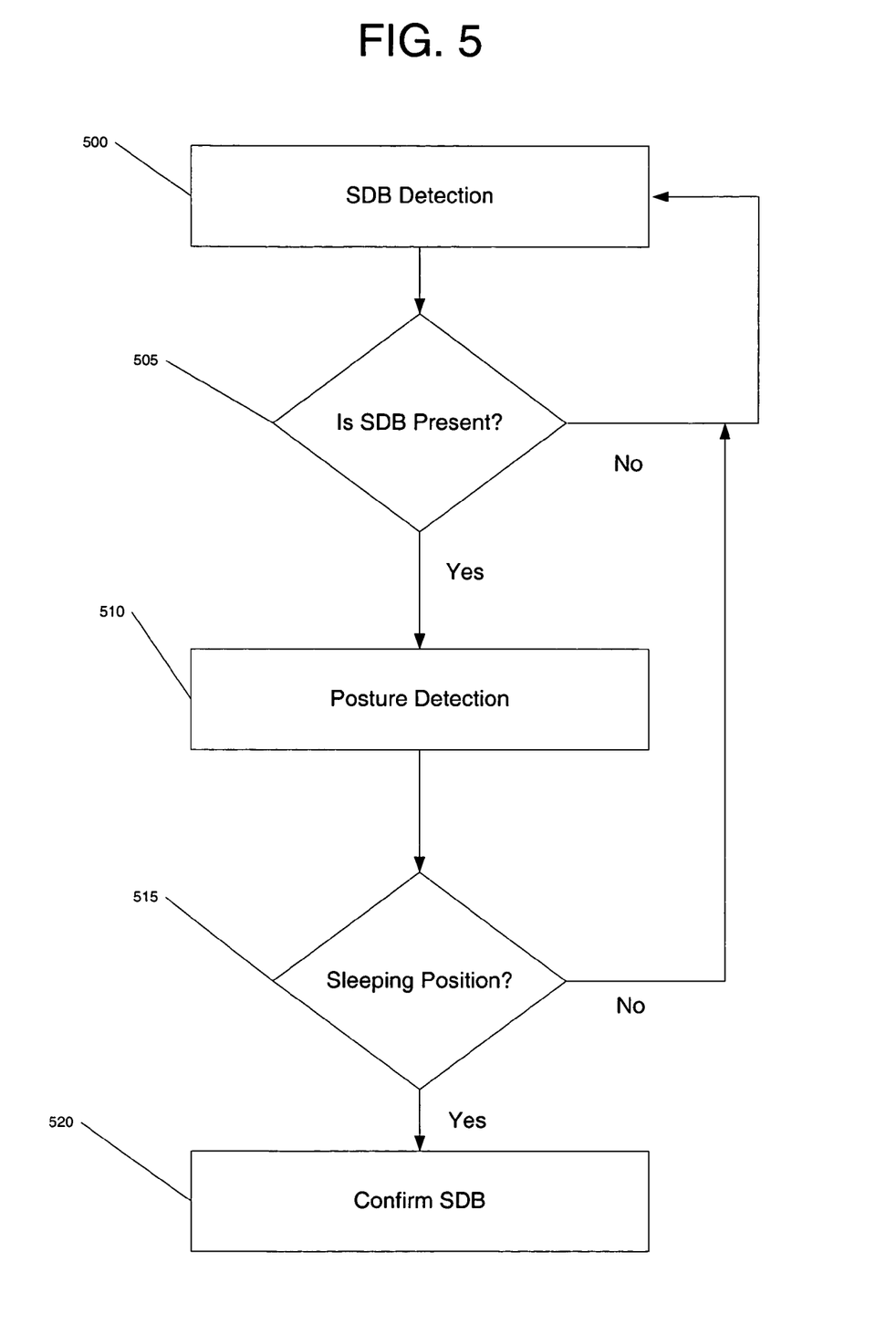
FIG. 5 is a flowchart illustrating a process for using position data to augment sensed SDB indicators.

FIG. 5 is a flowchart illustrating a process for using position data to improve the reliability of SDB detection. As previously discussed, the IMD 400 will sense one or more parameters that indicate, directly or indirectly, the presence, onset, or anticipated onset of an SDB episode. For example, breathing rates may be monitored and indicate apnea or hypopnea.

Thus, either on a continual basis or during programmed periods of time the IMD 400 is monitoring (500) for such SDB indicators. When some event or parameter is sensed, a determination is made as to whether the event or parameter is indicative of SDB. For example, the IMD 400 may sense a reduction in a breathing rate. The IMD 400 evaluates the particular sense event and determines (505) if it is indicative of SDB. If not, the process returns to (500) and the IMD 400 continues to monitor.

If the IMD 400 determines (505) that the sensed event is likely indicative of SDB, the patient's position is evaluated (510) based on data obtained from the position sensor (445). Though not illustrated, sensor data indicative of the patient's activity level could be used in combination with the position data or in lieu of the position data. The IMD 400 utilizes the position data and determines (415) if the patient is in a position normal for sleeping and/or if the activity level is indicative of sleeping. The particular criteria used can vary widely based on physician preference as well as the particular parameters sensed for SDB. Thus, the sensed SDB indicators will only be acted upon (520) as being indicative of an SDB event if the position sensor 445 determines that the patient is in a sleeping position and/or has an activity level conducive to sleeping.

For example, the IMD 400 may only confirm SDB is the patient is in a near horizontal position. Alternatively, the IMD 400 will confirm SDB if the patient is in any non-vertical orientation or if the patient is reclined beyond some predetermined angle. Of course, it is quite possible for a patient to sleep while sitting. As such, the appropriate criteria will be implemented if SDB is to be detected while the patient is in such a position. The use of the activity sensor alone, or in combination with the position sensor may provide a further means of confirmation. For example, a patient who is actively moving is presumed awake.

In this manner, events that are sensed that would otherwise indicate SDB may be further evaluated and only acted upon as relating to SDB if they are confirmed by the position and/or activity data. The occurrence of false positives is greatly reduced or eliminated. Once SDB is confirmed, the IMD 400 will take the appropriate action ranging from data recordation to the delivery of therapy.

As illustrated in FIG. 5, SDB data is sensed and when detected, subjected to confirmation. Alternatively, the IMD 400 could operate in a reverse format wherein SDB sensing only occurs when the position and/or activity data indicate that the patient could be in a sleep state. In such an embodiment, any sensed SDB data would then be presumed to be indicative of SDB as it was necessarily detected while the patient is determined to be in a sleep conducive position or activity level. Specifically, the data from the position sensor 445 toggles the IMD between an on state for SDB detection and an off state for SDB detection.

Figure 6:
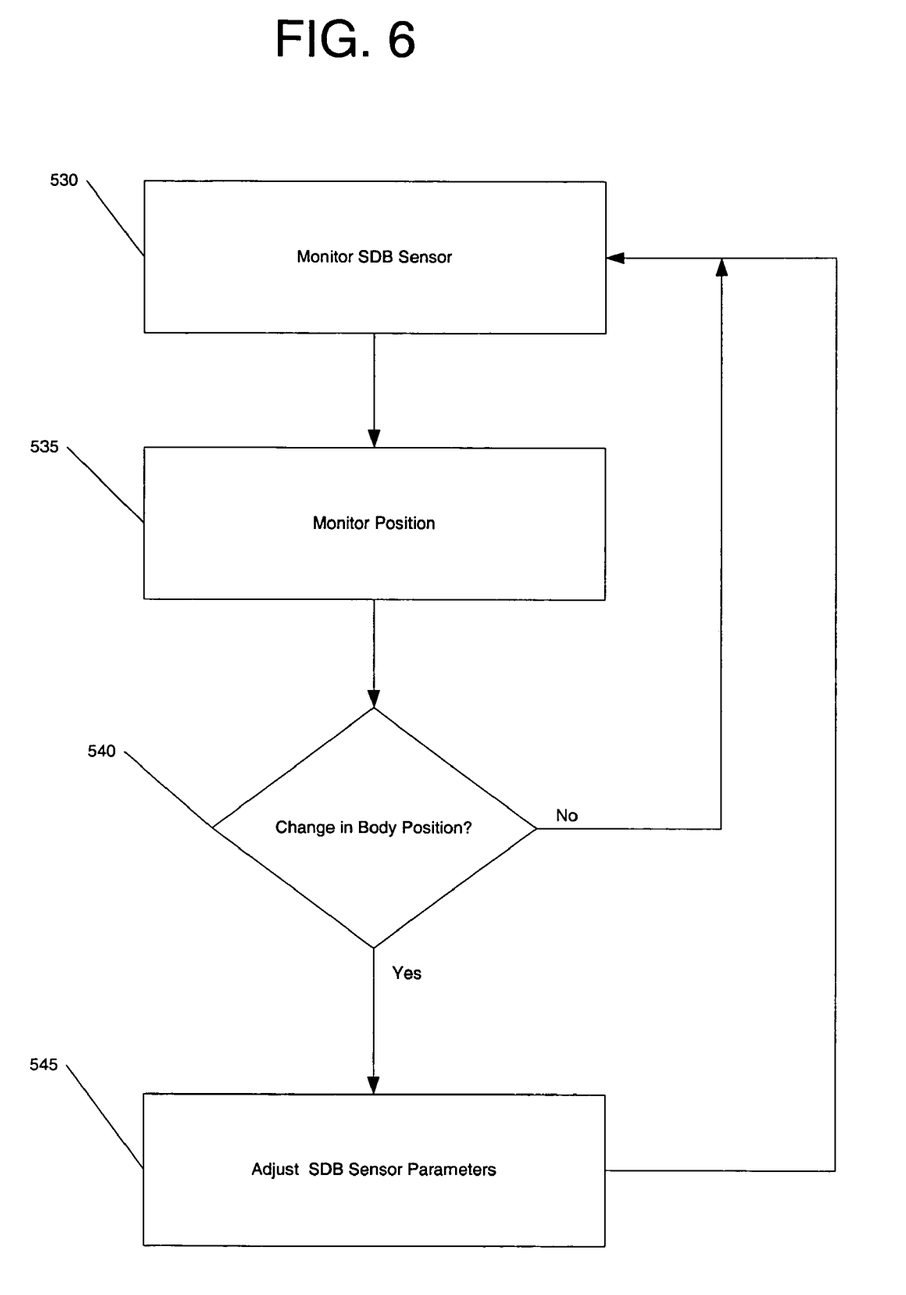
FIG. 6 is a flowchart illustrating a process for using position data to adjust SDB sense parameters.

FIG. 6 is a flowchart illustrating a process for using position sensor data to modify certain SDB detection parameters. Whether operating continuously or during certain predetermined periods of time, the IMD 400 monitors for SDB indicative events. The particular event or events that are being monitored can vary; however, the IMD will have specific programmed criteria for whatever is ultimately being monitored. For example, respiration rates below a predetermined level will be used as a trigger.

While the IMD 400 is ultimately monitoring, for example, the patient's respiration rate some specific physical parameter is actually being sensed. It is those physical parameters that are correlated to some pre-established criteria that ultimately indicate SDB. For example, while ultimately monitoring respiration a temperature sensor may be placed adjacent to the patient's airway. The onset and cessation of respiration produces resultant temperature variations that can be monitored and correlated to respiration. Likewise, an impedance sensor may be used to measure the impedance encountered by electrical current passing through the patient's upper body. The impedance will vary depending upon the expansion or contraction of the patient's chest due to the inspiration and expiration of air into and out of the lungs. This is a common technique for monitoring minute ventilation. Again, the impedance values can be correlated to respiration.

For a given patient, the measured impedance values for fully inspired or fully expired respiration will vary between some determinable values. However, these values are related to the patient's position during sensing. That is, one set of values is relevant while the patient is prone or supine while another set of values may be relevant while the patient lies on their side. Of course, other sensed parameters may likewise vary depending upon the patient's orientation during sensing. In addition, the patient's position affects noise levels for certain sensed parameters.

Thus, the IMD 400 monitors (535) the patient's position during the sensing of SDB criteria. The IMD 400 uses the appropriate criteria for evaluating the SDB sensed events (e.g., the particular range of impedance values) based on the patient's position. If a change is detected (540) in the patient's position, then the appropriate criteria for the new patient position are implemented (545).

The process of determining patient position to select an appropriate set of evaluation criteria for SDB monitoring may be used alone or in combination with the above described process for using position and/or activity data to confirm SDB sensed events.

Although the present invention has been described with reference to preferred embodiments, persons skilled in the art will recognize that changes may be made in form and detail without departing from the spirit and scope of the invention.

What is claimed is:

1. An implantable medical device (IMD) comprising:
   means for sensing a physical parameter relevant to sleep disordered breathing (SDB);
   means for sensing a patient posture;
   means for selecting criteria for evaluating the physical parameter, wherein the means for selecting base the criteria selection on the sensed patient posture; and
   means for determining if the physical parameter is indicative of SDB based on the sensed patient posture and according to the selected criteria.

2. The IMD of claim 1, further comprising means for sensing a patient activity level, wherein the means for determining determines if the physical parameter is indicative of SDB based on the sensed patient posture and the sensed patient activity level.

3. A method of using an implantable medical device (IMD) for the detection of sleep disordered breathing in a patient comprising:
   sensing a parameter indicative of SDB;
   determining an orientation of the IMD indicative of a posture of the patient;
   selecting a set of criteria to evaluate the sensed parameter, wherein the set of criteria is selected based on the determined orientation; and
   evaluating the sensed parameter according to the selected set of criteria based upon the determined orientation to determine if SDB is present.

4. The method of claim 3, wherein the set of criteria include impedance values.

5. The method of claim 3, further comprising:
   sensing an activity level of the patient, wherein evaluating further includes evaluating the sensed parameter based upon the determined orientation and the activity level.

6. The method of claim 3, wherein sensing of the parameter occurs prior to determining the orientation.

7. The method of claim 3, wherein determining the orientation occurs prior to sensing the parameter.

8. The method of claim 7, wherein the determined orientation toggles the IMD to sense for SDB when the determined orientation indicates a posture conducive to sleep.

9. The method of claim 4 wherein a first set of impedance values are utilized if the orientation indicates the patient is prone or supine and a second set of impedance values are utilized if the orientation indicates the patient is laying on his or her side.

10. An implantable medical device comprising:
    a microprocessor;
    a position sensor coupled with the microprocessor and providing data indicative of a patient posture;
    a sleep disordered breathing (SDB) sensor communicatively coupled with the microprocessor and configured to sense a physical parameter that is useful in monitoring SDB and provide data to the microprocessor indicative of the physical parameter, wherein the microprocessor evaluates the data from the SDB sensor in a first manner if the position sensor indicates a first position and evaluates the data in a second manner if the position sensor indicates a second position; and
    a memory containing a plurality of SDB criteria sets, wherein the microprocessor selects a given set of SDB criteria from the memory based ucon a specific position identified by the position sensor.

11. The IMD of claim 10, wherein the SDB sensor is an impedance sensor for monitoring minute ventilation and the criteria sets are impedance values.

12. The IMD of claim 11, wherein a first set of impedance values are selected if the position sensor indicates a prone or a supine position and a second set of impedance values are selected if the position sensor indicates a lateral position.

13. The IMD of claim 10, wherein the first position includes positions indicative of a sleep state and the second position includes positions indicative of a waking state.

14. The IMD of claim 10, further comprising an activity sensor communicatively coupled with the microprocessor wherein the activity sensor provides additional data to the microprocessor for selecting the first manner or the second manner.

* * * * *

UNITED STATES PATENT AND TRADEMARK OFFICE
CERTIFICATE OF CORRECTION

| | | |
|---|---|---|
| PATENT NO. | : 6,964,641 B2 | Page 1 of 1 |
| APPLICATION NO. | : 10/746814 | |
| DATED | : November 15, 2005 | |
| INVENTOR(S) | : Yong K. Cho et al. | |

It is certified that error appears in the above-identified patent and that said Letters Patent is hereby corrected as shown below:

Col. 14, line 32, delete "based ucon a" and insert --based upon a--

Signed and Sealed this

Third Day of April, 2007

JON W. DUDAS
*Director of the United States Patent and Trademark Office*